United States Patent [19]
Hock

[11] Patent Number: 6,119,516
[45] Date of Patent: *Sep. 19, 2000

[54] BIOFEEDBACK SYSTEM FOR MONITORING THE MOTION OF BODY JOINT

[75] Inventor: Allan G. Hock, Londonderry, N.H.

[73] Assignee: Advantedge Systems, Inc., Londonderry, N.H.

[ * ] Notice: This patent issued on a continued prosecution application filed under 37 CFR 1.53(d), and is subject to the twenty year patent term provisions of 35 U.S.C. 154(a)(2).

[21] Appl. No.: 09/084,440

[22] Filed: May 22, 1998

Related U.S. Application Data
[60] Provisional application No. 60/047,517, May 23, 1997.

[51] Int. Cl.[7] ........................................................ A61B 5/22
[52] U.S. Cl. ........................................ 73/379.01; 600/547
[58] Field of Search ........................... 73/379.01, 379.08, 73/379.09; 600/547, 587

[56] References Cited

U.S. PATENT DOCUMENTS

| | | |
|---|---|---|
| 4,108,164 | 8/1978 | Hall, Sr. . |
| 4,182,315 | 1/1980 | Vas et al. ................................. 600/500 |
| 4,413,629 | 11/1983 | Durley, III .............................. 600/453 |
| 4,665,388 | 5/1987 | Ivie et al. . |
| 4,667,685 | 5/1987 | Fine . |
| 4,986,280 | 1/1991 | Marcus et al. . |
| 5,107,746 | 4/1992 | Bauer ........................................ 84/626 |
| 5,146,929 | 9/1992 | Sawhill . |
| 5,354,050 | 10/1994 | McCarthy . |
| 5,373,096 | 12/1994 | Suzuki et al. ............................. 84/600 |
| 5,375,610 | 12/1994 | LaCourse et al. . |
| 5,607,361 | 3/1997 | Mastandrea et al. . |
| 5,797,803 | 8/1998 | Jung . |
| 5,823,886 | 10/1998 | Murray . |

OTHER PUBLICATIONS
Spine Tuner Instructions, Clear Sky Products 1997, Rev 5,1,97.

*Primary Examiner*—Max Noori
*Attorney, Agent, or Firm*—Vernon C. Maine; Scott J. Asmus

[57] ABSTRACT

A biofeedback system for self-monitoring of selected body motions includes configurable mounting appliances, compatible twist, stretch and flexure sensors, coded means for positioning and orienting sensors at any location of the body, and a small, self contained signal processing and feedback module. Multi-level instant audible feedback is employed to provide a quick learning environment. The motion sensors include low force, high compliance, long extension sensors.

14 Claims, 11 Drawing Sheets

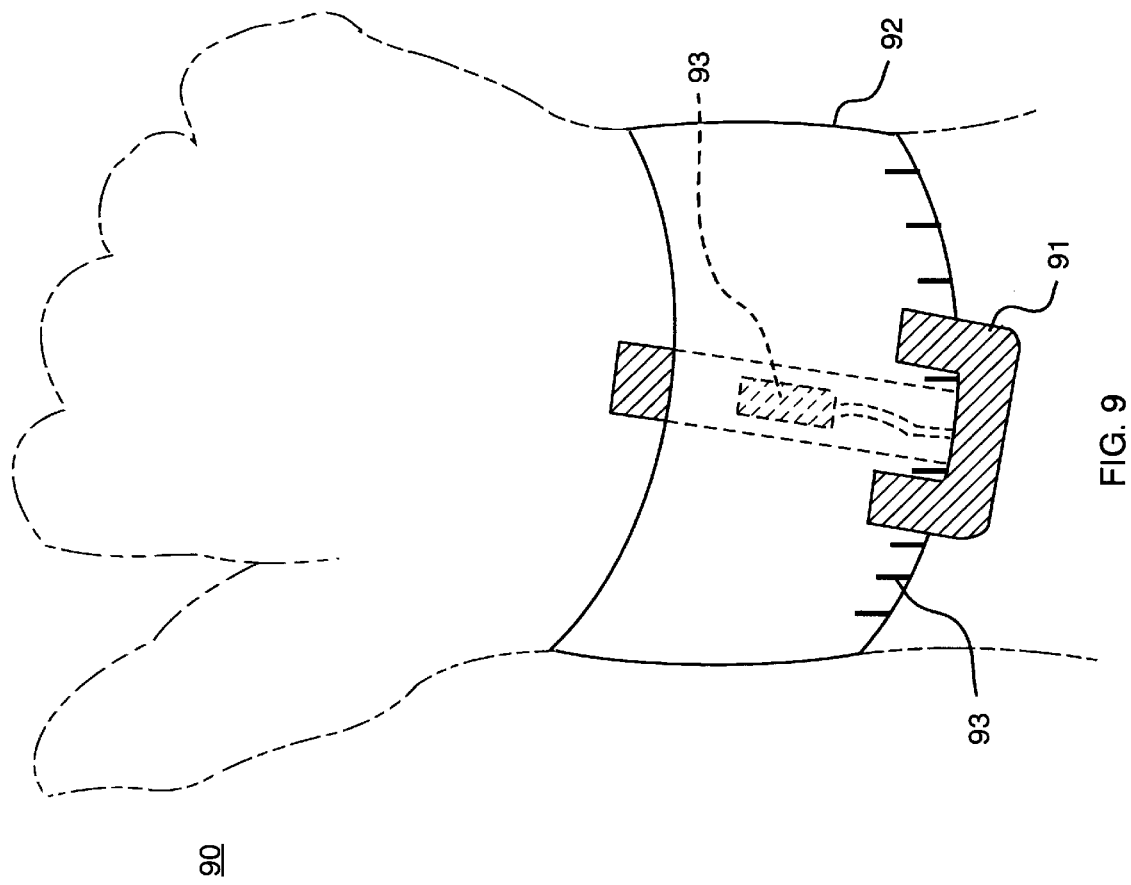

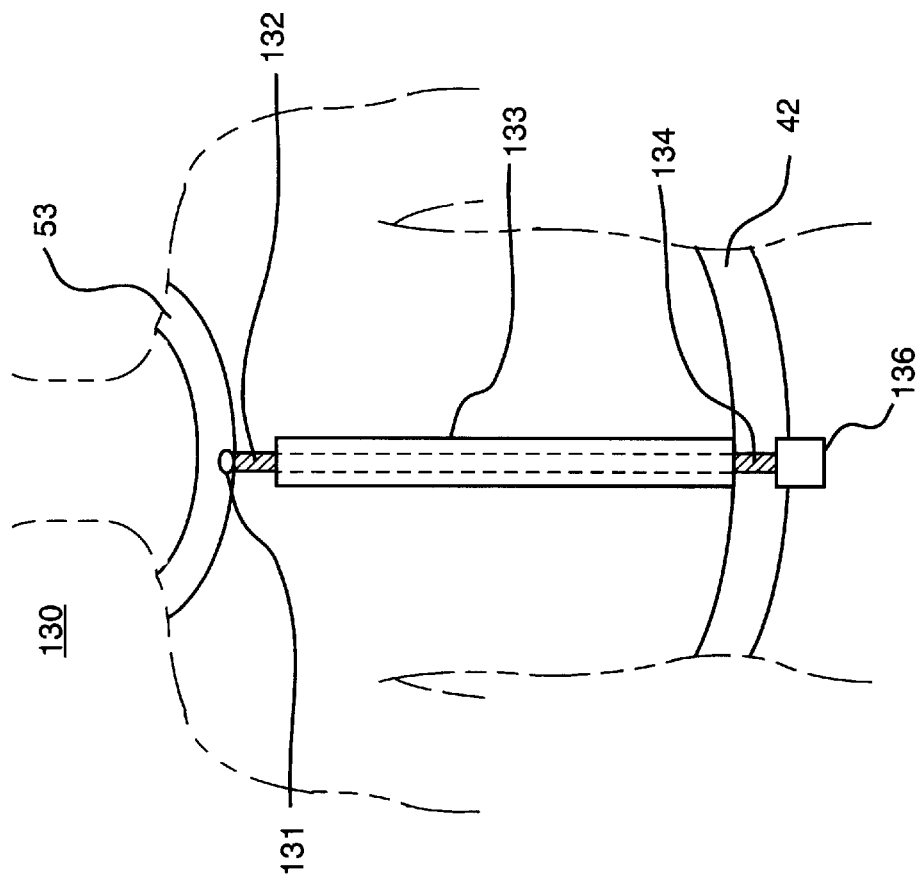

BIOFEEDBACK SYSTEM FOR MONITORING THE MOTION OF BODY JOINT

This application relates to U.S. Pat. No. 5,745,028, filed Apr. 29, 1994, and pending U.S. patent applications Ser. Nos. 60/047,517, filed May 23, 1997, and 09/010,019, filed Jan. 21, 1998.

BACKGROUND OF THE INVENTION

1. Technical Field of the Invention

This invention relates to instrumentation for monitoring of motion and flexure of body joints and real time biofeedback to the user. In particular, it relates to a system of body mounted appliances, sensors and specialized signal processors with audible and other biofeedback capabilities.

2. Discussion of Prior Art

The art of user fitment with medical devices for injury avoidance and rehabilitation therapy is not new. However, as with medical care and treatment in general, it used to be conducted with a somewhat cavalier attitude about cost. The 'if it doesn't cost a lot in can't be any good' attitude, was driven home to the applicant some years ago when a new state of the art oscillometer product costing a conservative $300 was offered to a surgeon who quipped, "I paid that for the light I wear in the operating room," and declined to consider it further.

Now, however, we have entered an era of great emphasis on reduction of medical care and treatment costs. There is a new willingness by the medical care delivery establishment to consider and even search for lower cost products that offer bonifide medical benefits. The need for lower cost medical products extends to injury prevention and rehabilitation devices.

There are at least two patented body suit implementations for general measurement of body activities for injury avoidance and/or rehabilitation. The first body suit, disclosed in U.S. Pat. No. 4,729,377, requires points of electrode contact with the skin and requires soaking the garment with conductive fluid to select the measurement points of interest. The second suit, disclosed in U.S. Pat. No. 5,375,610, encompasses the entire body and measures by a plurality of mercury switches. Both are costly examples of accomplishing generalized monitoring at the expense of ease of use and do not lend them selves to casual use as in sports training or for prolonged use in the field of action. These types of devices are more appropriate for specific data collection sessions rather than for everyday wearing to monitor body motion for injury prevention or rehabilitation in the industrial setting.

Professional and recreational training activities for kinetic sports share the requirement for low cost, effective monitoring of body motion. Common problems facing both industries are the need for a system or inventory of low cost associated devices to meet the needs of athetes and patients of different sizes; the need for a flexible scheme for universal fitments adaptable to each part of the body; the need for a self-monitoring system and methodology that is easy for the athlete or patient to remove and reinstall daily, and to use and interpret so as to realize the full benefit.

More specifically, industry data clearly indicates a large amount of pain, suffering, lost time and lost productivity results from back injuries that occur on and off the job from lack of training or improper training in lifting and related activities. Lifting is a general problem, and twisting while lifting or repetitive twisting such as when moving parts along a production line are statistically very significant contributors to employee injuries.

One example of a recently introduced body motion monitoring device is the Spine Tuner™ by Clear Sky Products, a posture monitor consisting of a belt that goes around the back approximately half way between the waist and shoulder that holds a small system module against the spine. The system module consists of a pressure activated switch that is actuated by pressure, forcing the housing to compress front to back, actuating the switch. When the switch is closed, a battery is connected directly to a small motor with unbalanced weight, to cause vibrations that are noticable to the user. The system sensitivity is set by adjusting the contact spacing on a stamped metal switch by turning an adjustment screw. This operation cannot be performed while the device is being worned, which requires the user to use an awkward trial and error approach to obtain a useful setting.

One example of the need for body motion monitoring in the sports training category is in golf. The new 'buzzword' in the golf industry for the last five years is the "X" factor, a rotation of the shoulders relative to the hips. The need to monitor spinal twisting in this instance is similar to the industrial requirements cited above.

It is common for workers in some companies and industries to be required to wear back support belts. Home DePot and the Merriot Chain are among companies with this requirement. Interviews with workers that are required to wear these belts produce answers ranging from, "Now that I have support I can lift heavier things", which defeats the purpose, or comments like "I have to wear it but I don't think it does anything." There seems to be an acceptance and confidence problem with these commonly required devices that defeats or reduces their intended benefit.

Much of the technology for medical and sports requirements rely on braces. A sport brace called The Secret™, endorsed by golf pro Greg Norman, sells at a premium price, but constrains the user to a particular position of the wrist, an approach that is not likely to promote good muscle memory.

Braces in general have a number of problems, they are uncomfortable, frequently they do not quite fit the subject or the need, in training they do not promote good muscle memory, they can cause injury by constraining too well during a required activity, particularly in athletics, and they can promote "false" confidence causing users to try to overperform.

What is needed, for both medical and athletic fields, is a low cost system and methodology of devices, sensors and biofeedback mechanisms that is flexible and adaptable to various body motions, comfortable to wear, and easy to understand and use.

SUMMARY OF THE INVENTION

A biofeedback system is herein disclosed that allows for a universal monitoring methodology to be applied to the physical therapy needs for the human body, by combining configurable mounting appliances, compatible motion sensors, coded means for positioning and orienting sensors at any location of the body, with a small self contained signal processing and feedback module. Multi-level instant audible feedback is employed to provide a quick learning environment. Motions of the back, torso, limb joints and digits can be monitored. Specific subset systems employing the concepts and methodology focus the back and a second subset focuses limb joints (wrist, elbow, knee and ankle). Special versions concentrate on proper lifting and on avoiding twisting of the back while performing common repetitive industrial movements that have a proven history of harming the performer.

To strengthen the system concepts, two low force, high compliance, long extension sensors have been disclosed. These enhance the functionality, simplicity and cost of the resulting system implementation.

An object of this invention is to provide a universal physical therapists biofeedback kit capable of providing the doctor or therapist with an in office fitting-breadboard that can be custom set and adjusted, for a number of different patients and for a number of different patient problems, then used as a final product that the patient wears out of the office.

An object of this invention is to provide mounting appliance systems allow motion sensors to be placed anywhere on the body with a chosen orientation and that is comfortable to wear and non-confining. Many of the athletic training devices on the market are uncomfortable constraining braces that force the user to a particular per-determined move that may not be correct for every user.

An object of this invention is to provide a monitoring system that allows a user to isolate on a single motion of the body (e.g. flexing the wrist in a particular plane), providing sensing and instant feedback to cue for proper motion performance and warn against improper motions. To promote proper training methodology including "one thing at a time" and natural learning.

An object of this invention is to include in the training system, a means for adjusting the system sensitivity to accommodate different levels of skill, performance, application or severity, in a manner that is simple to set up and adjustment. Many existing training systems for athletic activities compare and force the user to a pre-determined average motion.

An object of this invention is to provide a limb/body sensing and monitoring system that enables very low cost implementation. Medical systems that help a patient with recovery and rehabilitation, historically, have been expensive and frequently require fitting and ordering of a custom device. The disclosed invention provides a means for in office setup of the system so that the patient can leave with a properly fitted custom aid, and where the fitting breadboard and the final device are one in the same for cost and stock reduction.

An object of this invention is to provide training systems easy to wash, clean, or sterilize.

Further objects and advantages of this invention will become apparent from a consideration of the drawings and ensuing description.

BRIEF DESCRIPTION OF THE FIGURES

FIG. 9 is a perspective view of a wrist appliance and trident form sensor.

FIG. 13 is a back view of a person fitted with a belt and collar, with a belt mounted sensor base element and a connecting spinal suspender/sensor element.

DESCRIPTION OF THE PREFERRED EMBODIMENT

The invention is basically a biofeedback system for monitoring the motion of selected body joints. The appliances and sensors of the system are uniquely adaptable to fit individual users, for converting a selected motion or combination of motions of particular body joints into a particularized set of audible tones for coaching, warning and range of motion self-monitoring. The invention is susceptible of many variations. Accordingly, the preferred embodiments described hereafter should not be construed as limitations to the scope of the invention.

The preferred embodiments described herein utilize a common, self-contained electronic system signal processing and feedback module or subsystem (approximately 2"×2"× 0.75") that has a single system sensitivity adjustment control. The module is mounted or attached to any of the several universal mounting appliances, and is electrically connected to one or more system sensors. The module generates a limited sequence of stepped audible tones in response to sensor input, from which the incremental range of motion is easily interpreted. In the general case, an appliance set is selected appropriate the body joint of interest. The placement and orientation of a sensor on or within the appliance is guided by a coded scheme of markings or pockets, selectable depending on the motion of interest and easily identified in instructions for repeatability. The feedback module is connected to the sensor and mounted to the appliance.

Sensors are disclosed, that are mechanically soft (high compliance) elements that can measure motions over extended ranges and perform satisfactorily where developed forces may be very low. A variety of mounting appliances are disclosed, that together provide a one-to-one fitment capability for one or more of the various joints of the body, (i.e. there is a preferred appliance for the back, wrist, knee, etc.). Each appliance is universal in that it provides coded location or anchor points and orientations for mounting the sensor for the intended application. The coded location or anchor points facilitate a close description of the fitment and promote easy repeatability from written or verbal instructions.

The doctor, therapist, or user fits the system to a particular need by selecting planes of motion at the joint of interest via a sensor mounting point and orientation, and chosing the range of motion using the sensitivity adjustment. As the user moves through the range of motion, a limited sequence of stepped audible tones provide instant feedback with easily interpreted resolution. Alternate and addition forms of feedback may include lights, displays, vibration, and so forth. Position and motion data can also be transmitted between sensors or to a ground station data logger.

Preferred System Embodiment for monitoring the motion of the Back

Figure 6:
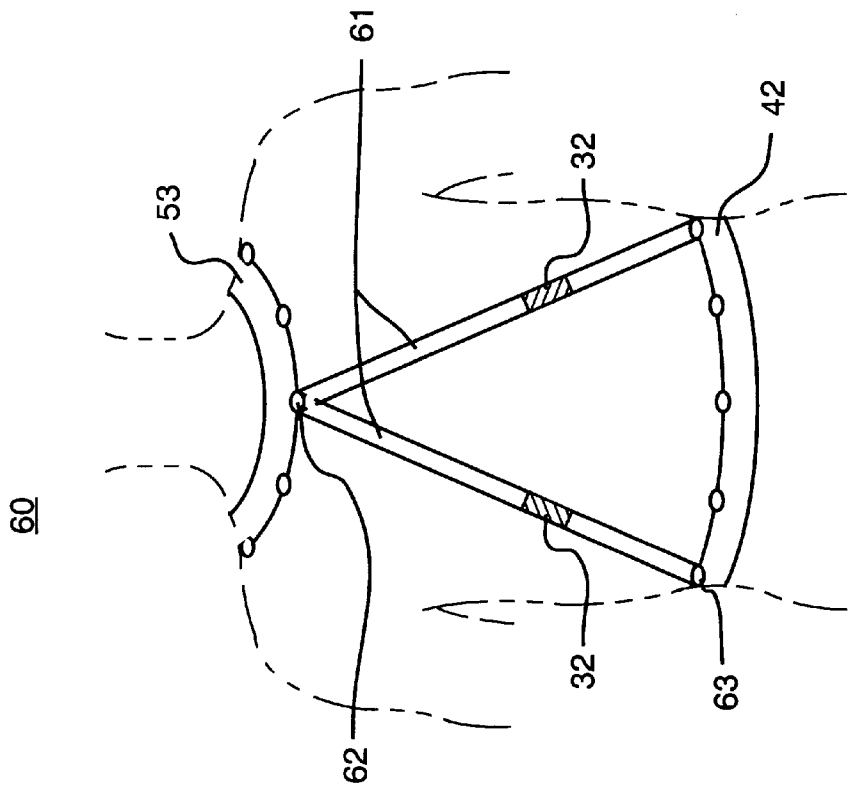
FIG. 6 is a back view of a person fitted with a belt and collar, each with multiple anchor points, and two connecting suspenders with sensors, configured in an inverted V arrangement.

Referring now to FIG. 6, there is disclosed a preferred biofeedback system embodiment of the invention suitable for monitoring the back and torso for twisting, windup, rolling, and hunching motions. Suspender system 60 includes suspenders 61, which are attached between collar 53 and belt 42, at selected anchor points 62 and 63. Suspenders 61 are configured with respective sensor elements 32, connected mechanically in series to carry the load of the suspenders in tension. Sensor elements 32 are electrically connected to the biofeedback module 143 of FIGS. 14 and 15, (not shown in FIG. 6), which in use can be mounted to belt 42. Sensor elements 32 may be specified to be compliant oval sensor 20 of FIG. 2, or a conventional sensor such as a potentiometer, encoder or switch. Alternate configurations for this application are shown in FIGS. 3, 4, 5 and 7.

Preferred System Embodiment for monitoring the motion of Limb Joints

Figure 10:
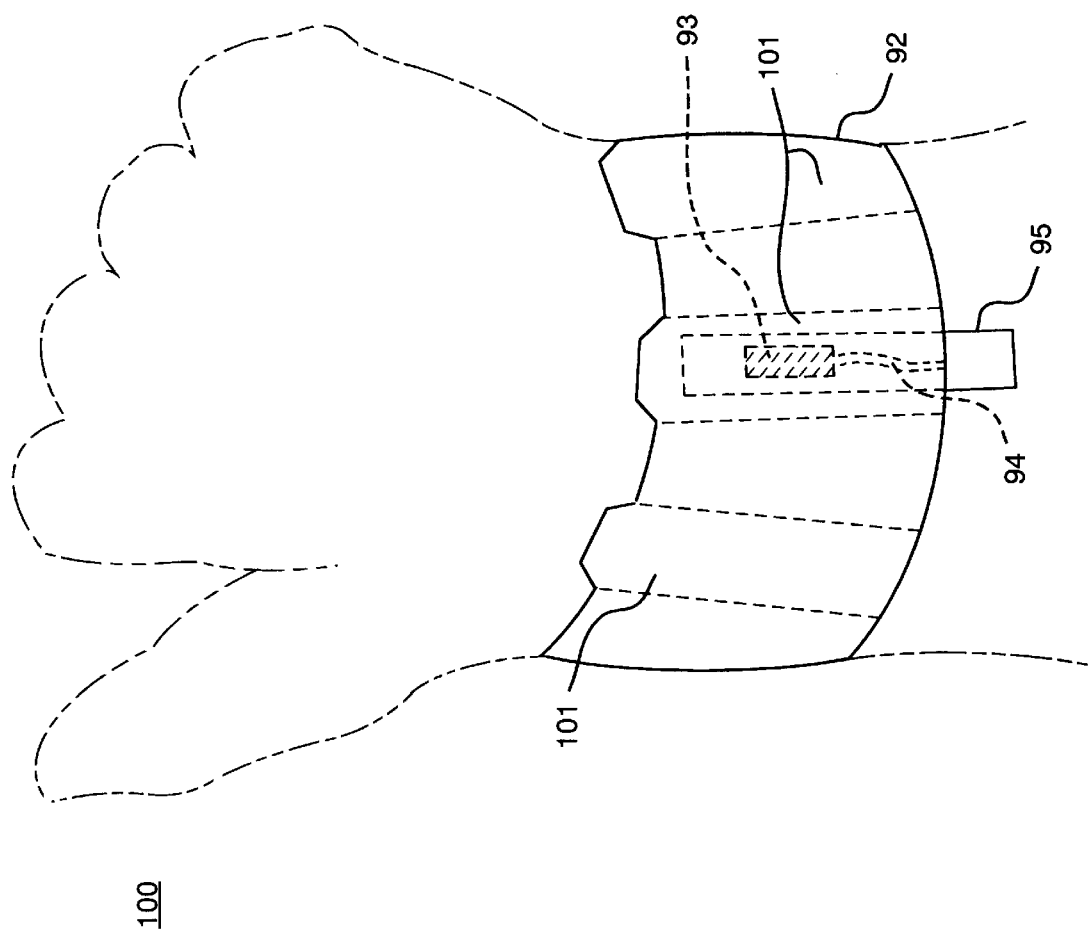
FIG. 10 is a perspective view of a wrist appliance with pockets and a flexure sensor emplaced in one pocket.

Referring now to FIG. 10, there is disclosed a preferred biofeedback system embodiment of the invention for monitoring the motion of limb joints, including the elbow, wrist, ankle and knee. Wrist joint system 100 includes wrist appliance 92 with coded mounting pockets 101, flexure sensor 93 mounted on shaped backbone 141, with signal leads 94 connecting to a signal processing and feedback module such as module 143 of FIG. 14 (not shown in FIG. 10). In practice, the biofeedback module would be attached to wrist appliance 92 in the manner illustrated in FIG. 14. FIG. 9 illustrates another system configuration variation for wrist motion monitoring.

Mounting Appliances

Figure 3:
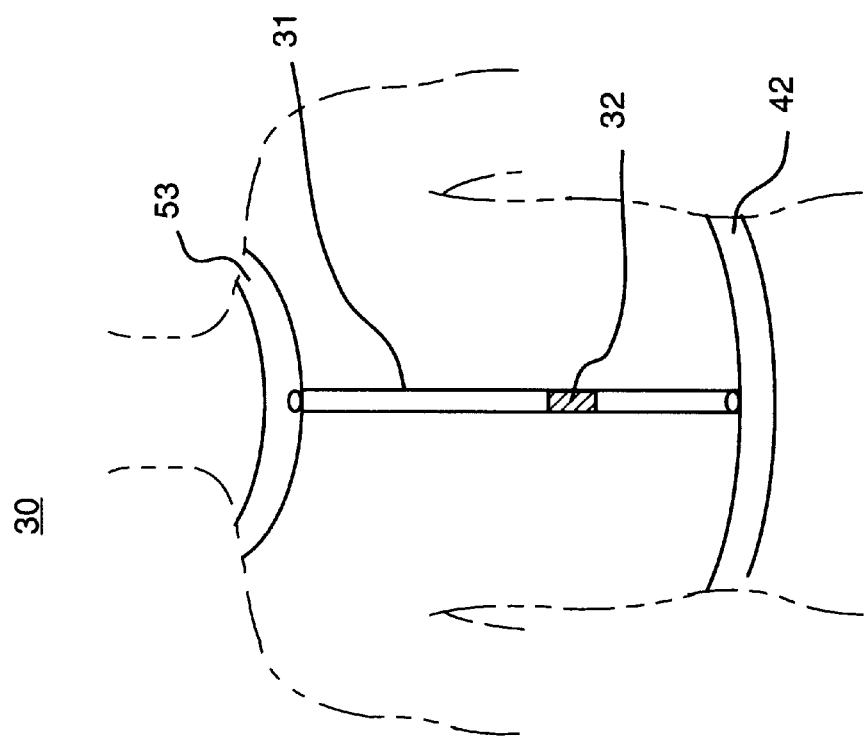
FIG. 3 is a back view of a person fitted with a belt and collar, with a connecting single vertical suspender with sensor aligned over the spine.

Referring generally to FIGS. 3, 4, 5, 6, and 7, suspender style mounting appliances are disclosed for use with suitable sensors for measuring various motions of the back and spinal column. Referring to FIG. 3, suspender system 30 consists of waist belt 42, collar 53, and connecting vertical suspender 31 configured so as to be aligned with the user's spinal column. Suspender 31 is constructed of an elastic material so as to stretch in compliance with the user's motion without noticable effort. Low force, large elongation sensor 32 is attachable to suspender 31 so as to be placed in tension in proportion to the linear extension of the suspender length.

Figure 4:
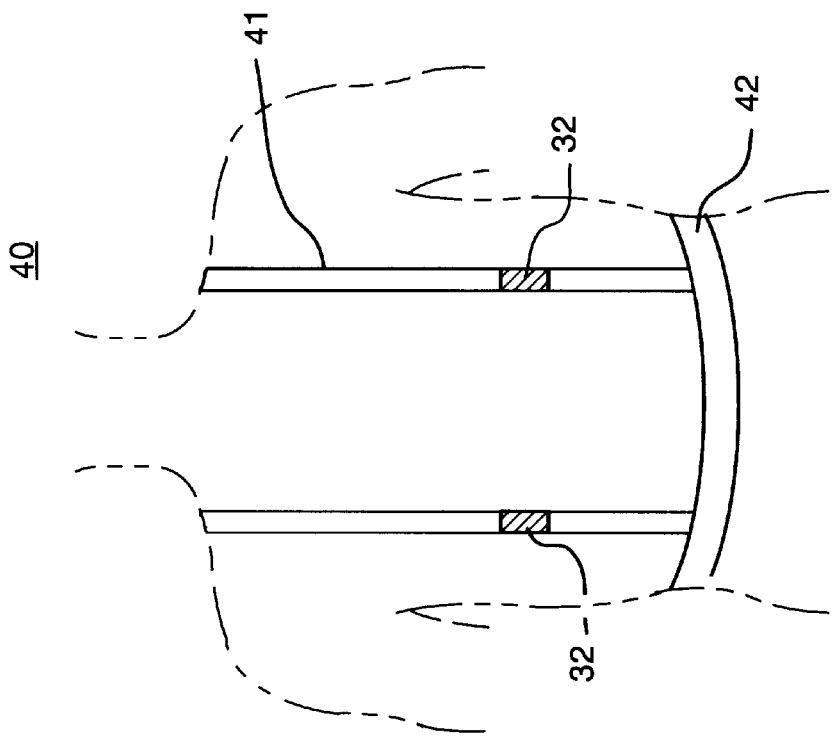
FIG. 4 is a back view of a person fitted with a belt with two vertical suspenders and sensors extending up over the shoulders.

Referring to FIG. 4, suspender system 40 includes belt 42 to which is attached a pair of over the shoulder suspenders 41. Suspenders 41 are constructed of an elastic material so as to stretch in compliance with the user's motion without noticable. Low force, large elongation sensors 32 are attachable to suspenders 41, the outputs connectable as a sum or different to a biofeedback module of the invention, to detect tilting or lifting of one or both shoulders.

Figure 5:
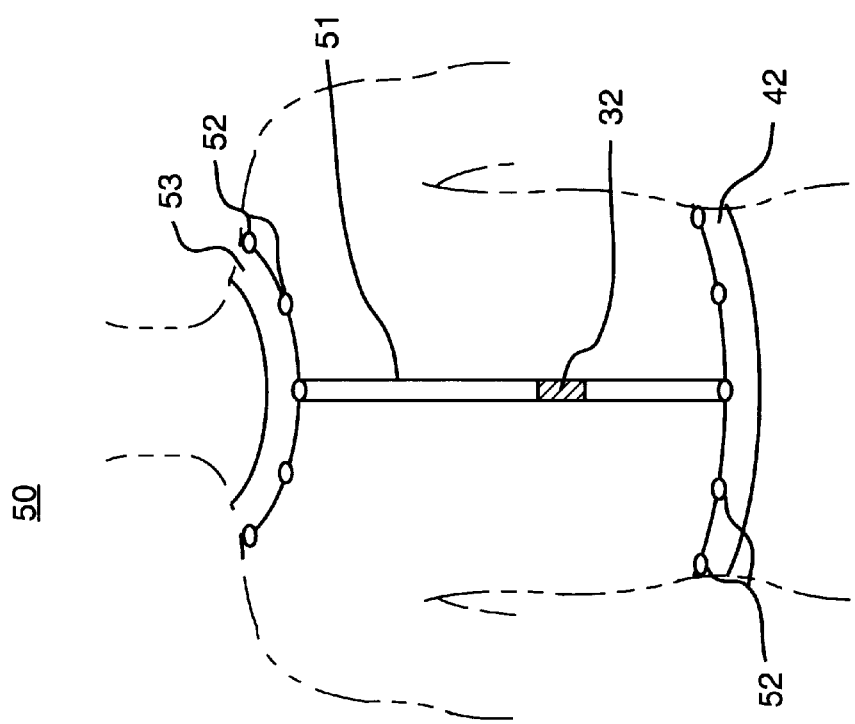
FIG. 5 is a back view of a person fitted with a belt and collar, each with multiple anchor points, and a connecting single vertical suspender and sensor.

Referring to FIG. 5, suspender system 50 includes belt 42, which is configured with multiple attach points 52 arranged at uniform intervals along its length. Collar 53 is similarly equipped with attach points 52. Suspender 51 is adjustable, stretchable, and connectable at any combination of belt and collar attach points to be aligned and compliant with the motion of interest. A low force, large elongation sensor 32 is applied to suspender 51 and connected to a biofeedback module of the invention in the manner described above. Suspender 51 is illustrated here in the over-the-spine, vertical position.

Referring to FIG. 6, suspender system 60 includes compliant suspenders 61, configured with respective low force, large elongation sensors 32, arranged in an inverted V form and attached at selected anchor points 62 and 63 between collar 53 and belt 42. Anchor points 62 and 63 are three of a multitude of selectable anchor points arranged at uniform intervals along the length of the belt and collar, each point coded so as to be easily designated in instructions or reports. As in previous embodiments, the sensors are electrically connected to a biofeedback module.

It will be apparent from the embodiments of FIGS. 5 and 6 that by choosing the appropriate anchor points and suspender elements, different motions of the back such as rolling, hunching, and twisting, can be selectively favored.

Figure 7:
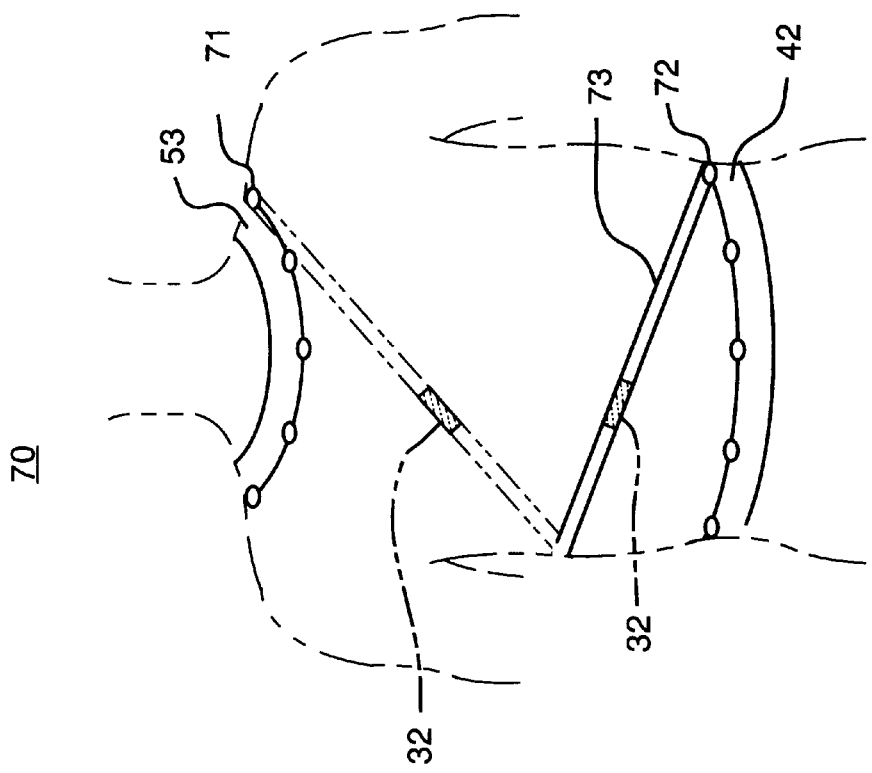
FIG. 7 is a back view of a person fitted with a belt and collar, each with multiple anchor points, and a connecting single suspender with sensors, configured in a diagonal, wrap-around back of belt to front of collar arrangement.

Referring to FIG. 7, suspender system 70 illustrates a variation on the systems of FIGS. 5 and 6, suspender 73 with sensor 32 being configured and attached to anchor points 71 and 72 on collar 53 and belt 42 so as to wrap around the torso of the user.

Figure 11:
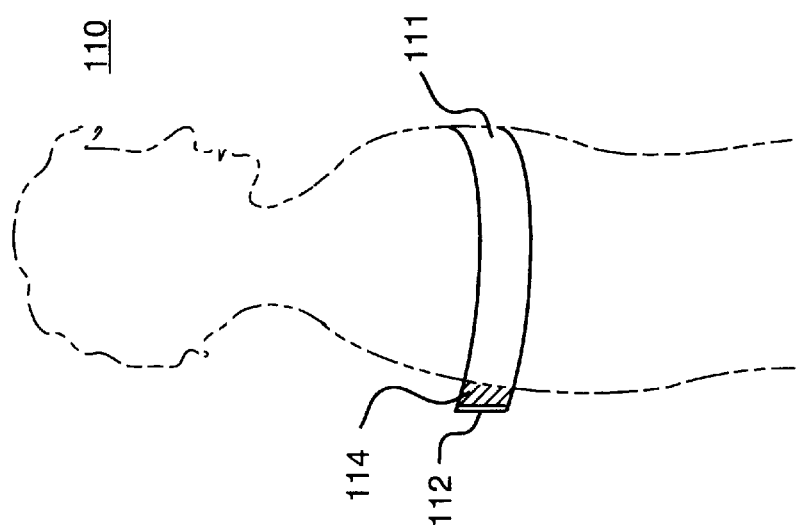
FIG. 11 is a side view of a person fitted with a chest belt appliance and back mounted sensor.

Referring to FIG. 11, back roll belt system 110 includes a belt 111 sized and intended to be mounted chest high on the user, to which sensor 112 can be mounted over the spine in compliant mass 114, so the sensor 112 is placed between belt 111 and the body. The sensor and operation of back roll belt system 110 is further described below.

Referring to FIG. 13, there is disclosed a back motion monitoring system 130, which includes belt 42 and collar 53 of previous embodiments, worn with anchor points aligned over the spine. The sensors and operation of back motion monitoring system 130 are further described below.

Figure 14:
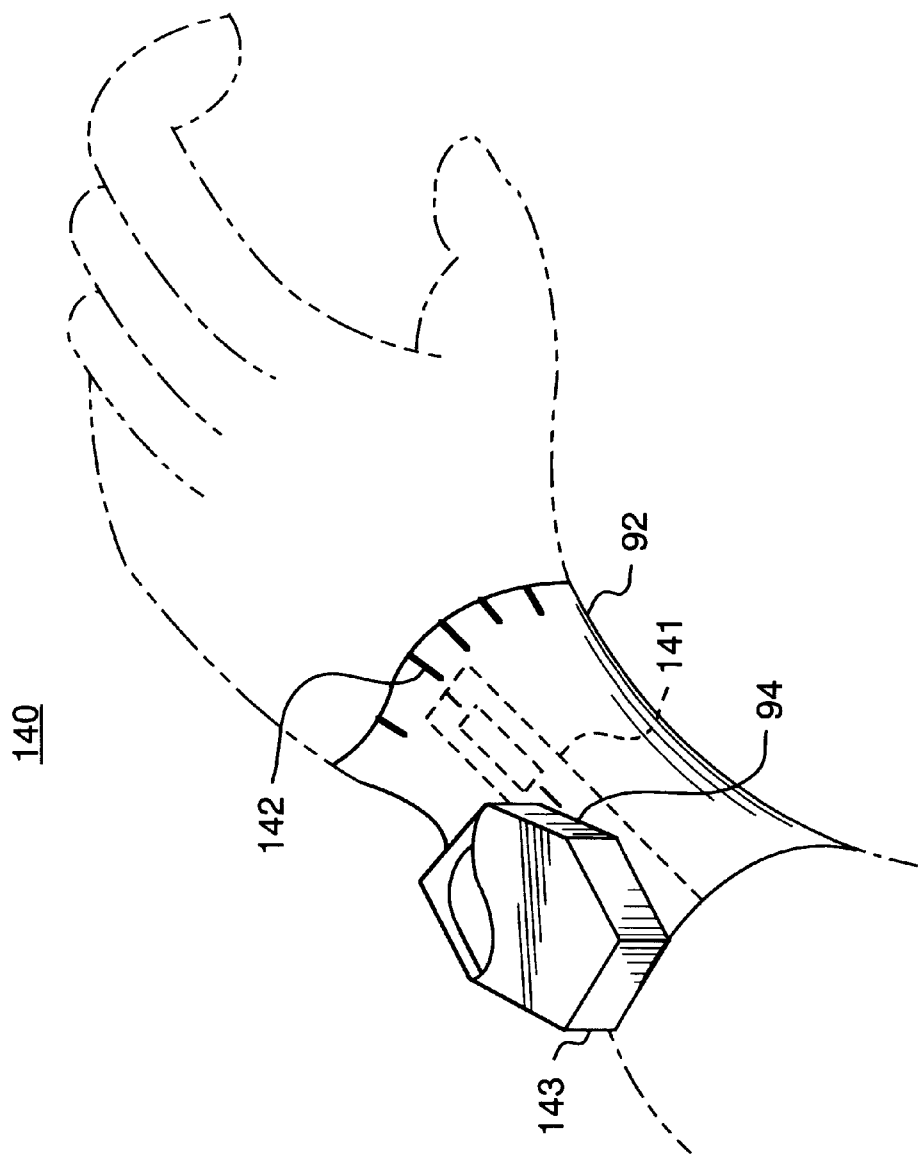
FIG. 14 is a perspective view of a wrist mounted appliance with sensor pocket, a flexure sensor mounted in the pocket, and a biofeedback module attached to the wrist appliance.

Referring to FIGS. 9, 10 and 14, there are disclosed wrist appliances that incorporate mounting options and coding for selection and placement of sensors. Wrist appliance 90 of FIG. 9 has coding marks 93 with which sensor 93 on trident backbone 91 can be selectively aligned. Wrist appliance 100 of FIG. 10 has coded pockets 101 into which sensor 93 and backbone 95 may be selectively fitted. In use, signal leads 94 are connected to a biofeedback module of the invention, which may be attached directly to the appliance.

Similar to FIGS. 9 and 10, wrist appliance 140 of FIG. 14 is configured with pocket 141 and coding marks 142. Biofeedback module 143 is attached by a clip to the wrist appliance and connected by leads 94 to a sensor in pocket 141.

Knee and ankle appliances of the invention closely correspond in construct and use to the appliances of FIGS. 9, 10 and 14, with mounting and coding features consistent with the details described above.

Sensing Elements

There are four distinct sensor systems that have been invented to accommodate the system compliance, coded mounting and low force high elongation needs of the system embodiments.

Figure 1:
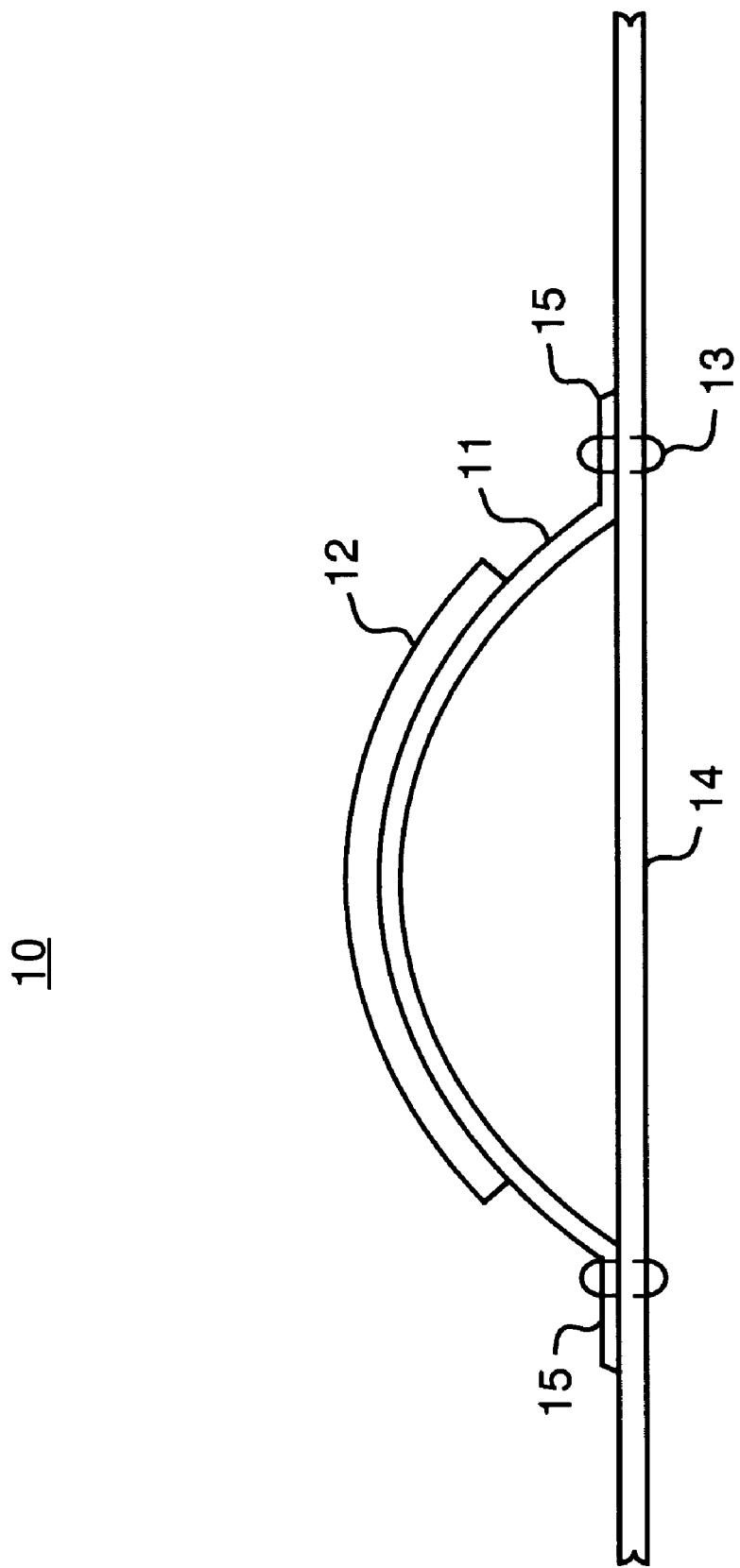
FIG. 1 is a side view of a compliant half oval link sensor mounted on a strechable belt.

Referring to FIG. 1, sensor system 10 is a compliant half oval link sensor consisting of half oval link 11, attached to flexible band 14 by fasteners 13, with a single sensor element 12 affixed to half oval link 11. Link 11 has spring-like response to tension applied at its end points, gradually straightening under increasing tension and recoiling to its original shape when the tension is released. Link 11 may be a plastic or metal member formed in the shape of a half oval, with attachment tabs 15 extending from each end.

Figure 2A:
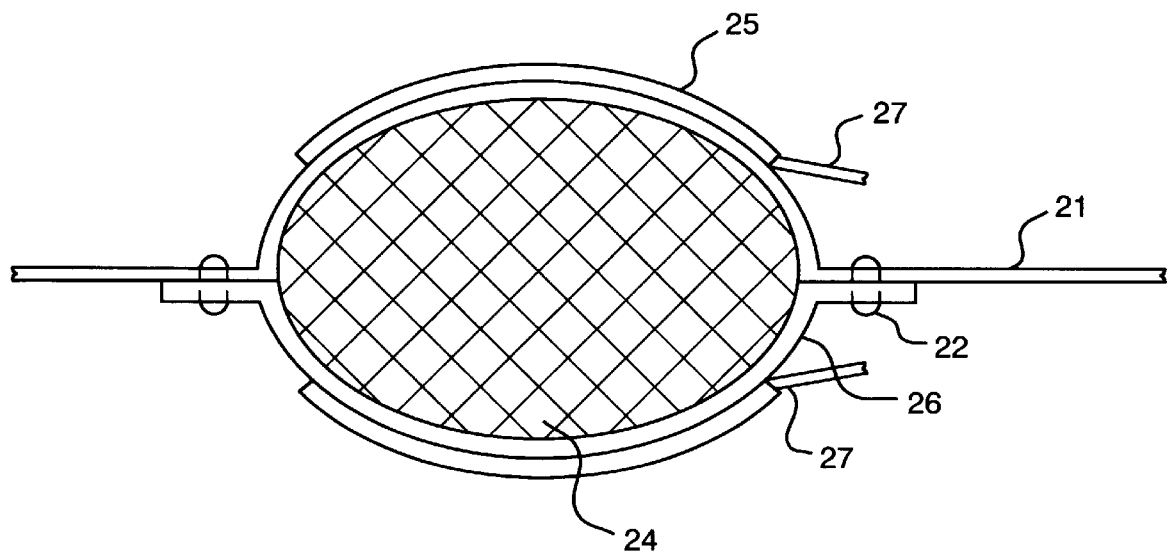
FIG. 2A is a cross section view of a compliant oval sensor mounted in tension between two belt sections.

Referring to FIG. 2A, sensor system 20 is a compliant oval sensor consisting of a flexible band 21 with a second flexible band 26 attached to it by fasteners 22 around compliant oval member 24. Oval member 24 is formed from a sponge-like compressible material that deforms readily under increasing band tension or lateral compression to an elongated form, but expands to its origin shape when the tension or lateral compression is released. Strain sensors 25 are affixed to bands 21 and 26 on each side of the oval; each having individual signal leads 27, which can be connected in aiding or opposing polarity to serve processing objectives in related multi-sensor configurations, or wired individually into a signal processing and feedback module of the invention.

Figure 2B:
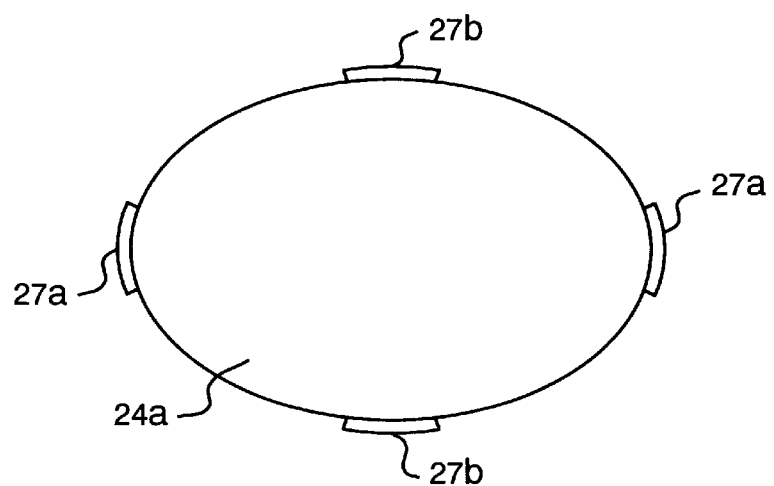
FIG. 2B is a cross section view of a compliant oval sensor with opposing end leads and opposing side leads embedded into the conductive mass of the sensor.

Referring now to FIG. 2B, compliant oval sensor 24A has two leads 27A embedded and extending from opposing ends and two leads 27B embedded and extending from opposing sides. It is constructed from a conductive elastomer that changes resistance with change in pressure (or tension), and is employed directly as the sensor element of a compliant oval sensor system similar in utility to sensor system 20 of FIG. 2. Suitable electronics and audio output capability and a battery may be embedded in oval sensor 24A or otherwised incorporated into a localized sensor system configuration, resulting in a fully self-contained sensor/biofeedback device that in combination with the appropriate appliance, functions in the manner of the invention.

Referring to FIGS. 8, 9, 10 and 14, as has been disclosed in earlier applications by this applicant, the flexure sensors illustrated consist of a strain gage instrument beam, piezoelectric sensor or other means for measuring flexure over a relatively large area. In the current embodiments, Kynar piezoelectric film is used and the sensing area is approximately 0.4 by 1 inch. The area measured can be extended by increasing the beam dimension, the sensing dimension or both. It is also possible to instrument the beam with other variable resistance elements, magnetic systems and the like, all within the scope of the invention.

The bending beam or backbone of the various sensor assemblies of the invention can take the form of a simple rectangle, coded and sized to fit into the pockets of the various appliances of the invention. Alternatively, a trident form of sensor backbone, as illustrated in FIG. 9, provides a convenient form factor for fitment to some belt-like appliances.

Figure 8:
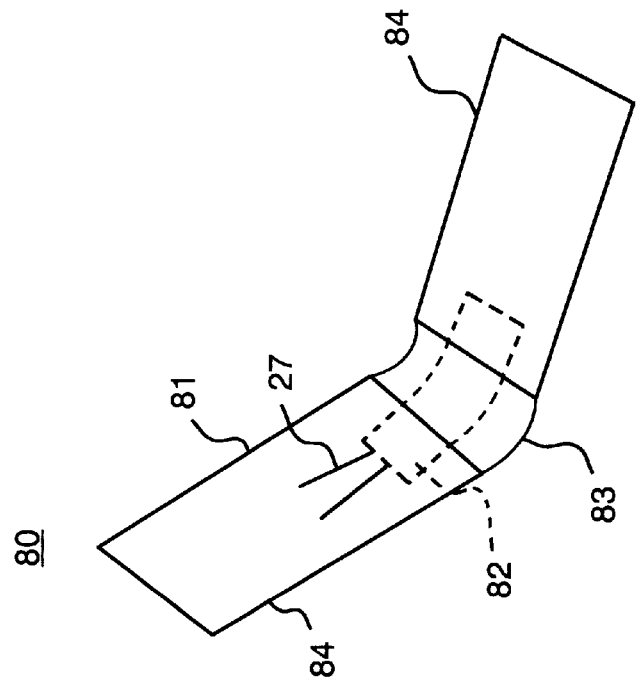
FIG. 8 is a perspective view of a hinge motion sensor element and base assembly.

Referring to FIG. 8, to enable the hinge-like action of hinge sensor system 80, sensor element 82 is mounted on backbone 81, and has leads 27 connectable to a biofeedback module of the invention. Backbone 81 is preconfigured for compliant bending at its central zone 83, with stiffer end zones 84 that are secured to the respective members of the joint of interest.

The flexible mounting appliances and methodology of the invention are also adaptable to accomodate conventional sensor elements such as strain gages, switches, potentiometers, and encoders. However, the sensors disclosed herein significantly enhance the functionality and help meet the invention objectives of low cost implementation, comfortable to wear and easily sanitizible. Rotary potentiometers and encoders are desirable sensors for integration within certain system configurations to measure rotation or twisting of the back or wrist, as for variants of the several embodiments disclosed in the figures.

Addition embodiments for monitoring back motion

Referring again to FIG. 11, back roll belt system 110 is a more specific implementation of the invention for measuring rolling of the back such as in lifting a weight from the floor. Sensor 112 and compliant mass 114 may be the compliant oval sensor system 20 of FIG. 2, or the compliant oval sensor 24A of FIG. 2A, or another flexure sensor mounted in a specially shaped sponge-like mass and placed between belt 111 and the body. The compliant characteristic of the sensor installation acts to integrate out the "noise" component of the motion or flexure signal that results from irregularities in the spine or in the placement of the sensor on the spine, making the location and orientation of the appliance and sensor less critical. The output of the sensor is connected to a biofeedback module of the invention.

Referring to FIG. 13, there is disclosed a back motion monitoring system 130 configured for isolating and measuring twisting motions of the back. The system includes belt 42 and collar 53 of previous embodiments, worn with anchor points aligned over the spine. An absolute position sensing rotary switch 136, which may be an encoder or potentiometer, the stator of which is attached to belt 42. Motion transfer strut 132 extends from the rotor of rotary switch 136 to collar 53 at anchor point 131, and is encased in a guiding shroud 133. Rotary motion is transferred between the upper body as referenced by collar 53 and the lower body as referenced by belt 42 to absolute position sensing rotary switch 136, and hense to a biofeedback module of the invention.

An alternate configuration of the back motion monitoring system of FIG. 13 for monitoring linear contraction and extensions of back bending, incorporates a static overlay cabability that provides one or more absolute position references which can be used to reset an integrator or zero out drift in a dynamic measurement systems such as the compliant oval sensor system of FIG. 2A. Referring again to FIG. 13, but in the context of a static overlay device, the body of switch 136 is connected to belt 42. One end of motion transfer strut 132 is connected to collar 53 at anchor point 131, and the other end is slideably connected to switch 136 so that the switch is acutated when the transfer strut reaches the predetermined reference position. Shroud 133 restricts and protects transfer strut 132 from bucking under compression as in an autothrottle cable assembly.

Signal Processing

Piezofilm sensors offer the best fit to the objectives of this invention, however there are disadvantages to the piezofilm sensors, they do not have static or d.c. response. While the low frequency response can be very low, 0.01 hz or less, practical considerations move this lower limit to the 0.1–0.3 hz range. Two mechanisms 1) dynamic compensation and 2) a static overlay system, overcome this disadvantage, and can be combined with the measuring systems to significantly improve performance.

1) Dynamic compensation:

The inherent non zero low frequency cutoff in piezofilms will, the magnitude of the signal lags the actual by a calculatable amount. Said lag or time droop in incoming signals can be compensated for by analog signal processing or by numerical means within signal processing and feedback module 143 of FIG. 14. However the static overlay system 130 FIG. 13 (disclosed below) offers a significant alternative.

2) Static overlay system:

It is common practice to use signal and or integrator reset circuits to yield quasi-static or quasi-d.c. response. When a system is not capable of zero frequency response, drift and signal lag occur. Integration of offsets and a.c. coupling and non static sensors preclude true static (zero frequency) response. Reset switches are commonly used to establish a new absolute reference at a point(s) in time or position.

Note that the static reset system shown in FIG. 13 can be used alone to provide a single point of reference. Also, the switch can replaced by a linear potentiometer or a linear encoder (indexed incremental or quadrature) to function as an absolute analog system over a limited range. It is however, very effective as a low cost static overlay that is used with one of the dynamic systems disclosed in the other figures. When these systems are combined there is good synergy. The dynamic system provides necessary refinements of signals for early warnings to be sounded so that an improper lift is aborted or a range of motion is not exceeded. The static overlay cabability reinserts a static reference and can be used to provide an absolute limit. While a dynamic sensing system with static zero frequency response could be used, the combined non-zero response sub-system in concert with the static overlay sub-system is a much better choice for the system inventions disclosed herein.

Adding Fuzzy Logic and AI (artificial intelligence)

The system elements and system configurations discussed to this point are very effective in measuring most motions that would be useful to monitor. There are specific motions that are subject to many extraneous inputs from "motion noise" sources. The methodology discussed above uses multiple sensors, symmetry and selective attachment to sort out the particular motion that one desires to monitor. Sometimes however, the extraneous motions are at a level where still more discrimination is needed. It is disclosed that AI (artificial intelligence) and Fuzzy Logic algorithms can be used to separate the signal from the noise. These algorithms would employ A-priori knowledge of the application and empirical data derived from directed experimentation to study the signals and rule out "probable noise".

Consider the application where the design intends to measure back motion during a lifting operation to detect improper technique. The system determines that the lifter is rolling his back to pick up an object rather than to keep his back straight while using the legs for the lift. The system monitors the motion, makes a decision, and sounds warning tones if an improper lift is about to be performed. Such a system can be used to train new employees to develop correct technique, or can monitor them continuously where risk is high, to sound a warning each time an improper lift is attempted. In this application there are many sources of motion that are not important to lifting, however these sometimes cannot be eliminated from the sensors measurement and therefore will appear in the output signal. The output signal is being monitored to make a decision to sound a warning tone.

What intelligence can be employed to minimize false alarms? The sources of motion noise can include: breathing, raising hands over the head, twisting, vertical roll of the shoulders, hunching of the shoulders, or unusual body configurations such as a particularly large stomach. To come up with a reliable monitoring system in the presence of these "motion noise" factors, intelligence applied to the resulting sensor signal may be required. The intelligence can use A-priori information and make judgements about the probable cause.

Figure 12:
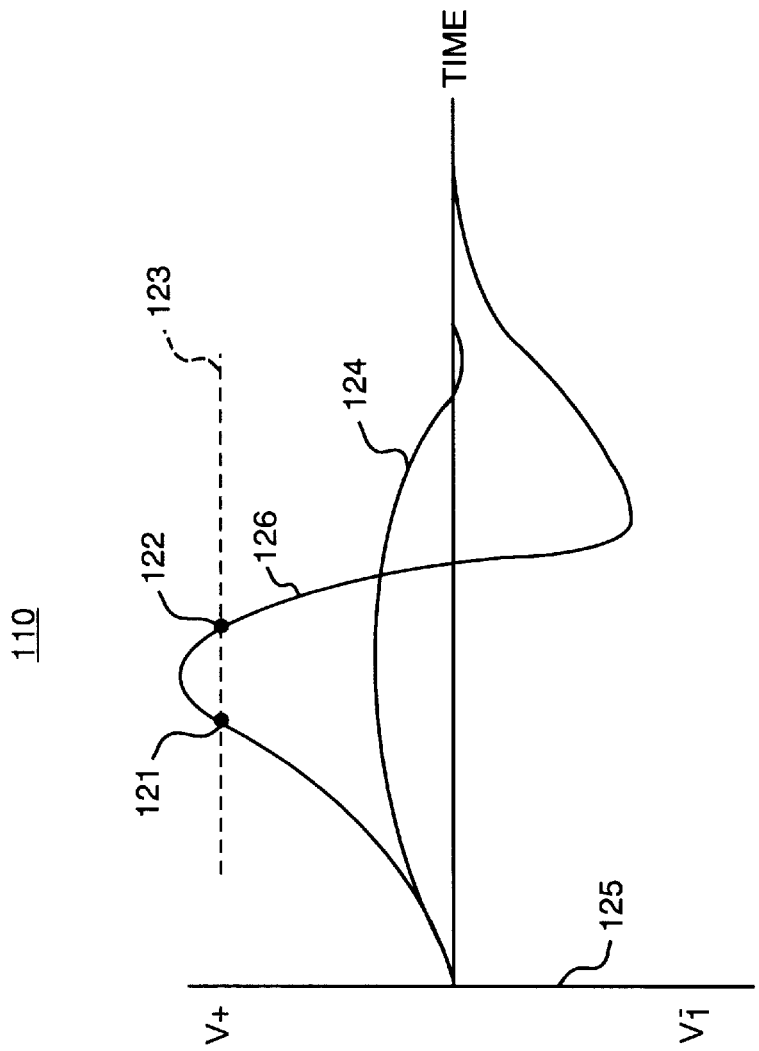
FIG. 12 is a graph of a model sensor signal and module response characteristic.

Referring now to FIG. 12, there is disclosed a model graph demonstrating some of the signal characteristics used by the biofeedback module electronics to improve the measurement discrimination, quality and applicability of the sensor inputs.

Voltage versus time curves are illustrated for lifting signal 126 and arm position signal 124. In the simplest case a peak motion threshold 123 is applied to lifting signal 126, sounding a warning that an improper lift is about to be performed. Further discrimination can be had by comparing the length of time that lifting signal 126 is above threshold 123 by examining the time between points 121 and 122 of the signal, making a decision only if the signal is above the threshold 123 for the correct range of time. This can avoid occurrence of a significant number of false alarms.

More protection against false alarm warnings can be attained by considering the characteristics of both the lifting signal 126 and the arm position signal 124. For this method of discrimination the electronics makes sure that both lifting signal 126 is above its threshold 123, and that the arms are in the lift position as determined by arm position signal 124, where a warning tone would be aborted if the arm position signal 124 was positive. Various conditions can be applied to one or more signal waveforms to improve the biofeedback system performance significantly.

Feedback and Data Collection

The preferred embodiment of the invention disclosed herein uses instant audible feedback. The feedback is in the form of stepped tone pitches that correspond one-to-one with selected or programmed signal thresholds. The tone that corresponds to the greatest motion threshold reached is held for a fraction of a second (0.1 to 0.5 sec). The effect of holding the peak motion is that the method assures that the user can both remember and make sense of the feedback.

The signal spacing between thresholds can be linear or non-linear so that early warning, or degrees of warning, can be achieved when an undesired body movement is occurring. It can be in bands so that training can be aimed at a central point. The feedback can take any other usable form either separately or in parallel with the audible feedback.

The information collected by the system can also be transmitted to a data logger or ground based computerized data collection system for post analysis and for establishing norms and correlating motion histories with future injury or other physical problems. Statistical data collection can be performed as a histogram of threshold events.

The preferred embodiment uses five tones, however more or fewer are possible, the resolution of the collected data corresponds to the number of thresholds and feedback tones. The Applicant's research indicates that a methodology using a relatively few descrete tone steps is significantly easier for the average person to detect, resolve and remember on a real time basis, than are continuously varying or many incrementally small step changes in frequency or amplitude.

Figure 15:
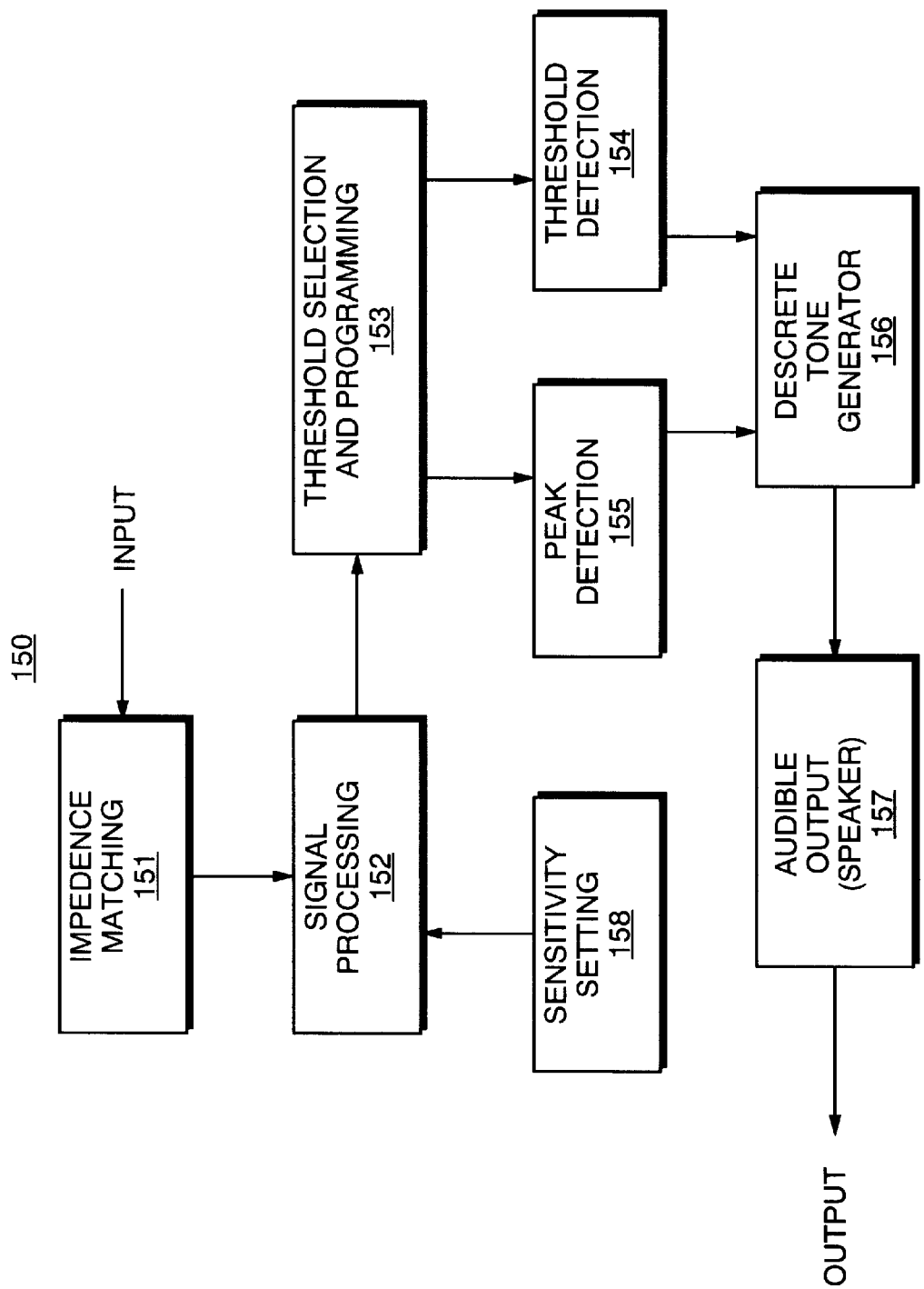
FIG. 15 is a block diagram of the signal processing and feedback circuit of the biofeedback module of FIG. 14.

Referring here to FIG. 15, a block diagram of the preferred embodiment of the system electronics of the signal processing and feedback module of the invention is disclosed. An input signal from the sensor would connect to impedance matching block 151, the output of block 151 is connected to signal processing block 152, which in turn connects to threshold selection and programming block 153. The output of block 153 feeds to both the threshold detection block 154 and the peak detection block 155, both block 154 and 155 outputs connect to the discrete tone generator block 156 which drives the audible output or speaker block 157. A sensitivity control block 158 allows the user to set the system gain and sensitivity by rotating the knob, the output of the sensitivity block 158 is connected to signal processor block 152 to accomplish this.

The circuitry necessary to accomplish the functionality of the biofeedback module is easily achieved by anyone skilled in the art, and need not be elaborated on here.

Operation of Invention

In operation, the system converts motions to multi-level audible feedback. Research has demonstrated that the multi-level instant feedback has the attribute of providing a memorable history of an event that might otherwise be too fast to be able to make a connection between the desired effect and the feedback. The methodology of the system integration provides total measurement flexibility encompassing back and torso, as well as for limb joints and digits.

A large part of the gain of measurement flexibility comes from the concepts imbedded in the mounting appliance. Each system has a mounting appliance that supports all of the measurements that one would want to make for the wrist or the back or other points where complex motions are possible. The appliances are soft and comfortable to wear, they are fitted with coded attachment points for sensors or for other members of the mounting system (e.g. an elastic suspender strap can be attach to a number of location on a belt or collar). The coding for the placement and orientation of the sensor on the mounting appliance might take the form of a Velcro strip upon which a mating Velcro strip affixed to the sensor can be aligned, or the use of placement marking which may be color coded can be incorporated into the mounting appliance, or the mounting appliance may be fitted with multiple pockets for the sensor to be fit into, where the selection of the pocket automatically selects the point of placement of the sensor and its orientation. The support electronics in its preferred embodiment takes the form of a signal processing and feedback subsystem or module, which at 1.4 ounces and approximately 2"×2"×0.75" can be attached directly to the clothing or to a convenient place on the sensor mounting subsystem, yielding a self-contained system.

One version works as a modified pair of suspenders, by removing restrictions on where the bands go on the body, as in FIGS. 3–7. The user or therapist card isolate one specific mode of movement (e.g. twisting of the back or pronation of the wrist) while ignoring the other motions that are occurring. This isometric selection can be further enhanced through the use of multiple sensors and by connecting them in different ways and processing the, information accordingly (i.e. the sensor can be connected in series or parallel, or they can be connected in a polarity opposing or polarity additive mode).

The signal processing and feedback module can be factory set to have specific dynamic frequency response that helps to enhance the activity that is being targeted for training by sorting out "noise" motions that occur but are not a part of the training. The sensitivity of the electronics can be adjusted through a wide range to account for differences in application and to account for wide differences in skill level or motion capability of the user.

The advantages of all of the subsystems described herein, including the mounting appliances, sensors, and signal processing and feedback electronics, work together to meet the numerous objectives of the invention.

The suspender system depends on a balance of compliant members to function properly, to this need, the compliant sensors described were invented. These elements convert low forces in the elastic suspender straps into a deformation of a half oval or full oval member which can be instrumented with large area strain gages. A system that is easy to use, comfortable to wear and does not impede the performance of the activity results from the application of the principles.

The invention is susceptible to many varations, all within the scope of the appended claims. For example, there is an appliance system for mounting the sensors of a biofeedback system that converts a selected body torso motion into audible tones, where the appliance system has multiple components, each component having at least one coded anchor point, the components being configurable on a user's body for establishing a suitable reference line for placement of a sensor relative to the desired motion.

As another example, the multiple components of a system may include a collar, a waist belt, and at least one interconnecting member attachable to the waist belt and the collar at the coded anchor points. The interconnecting member may be configured to accept the mounting of a sensor.

As a further example, the sensor may be a spring member that deforms under tension and reforms when released, with a measurable electrical impedance that varies with the degree of deformation applied to the spring member, and electrical leads by which the impedance can be measured.

Further, the spring member may be a half oval shaped structure the ends of which are attached to an elastic base member that would be subjected to a tension load, and the electrical impedance may be a strain gage sensor bonded to the half oval shaped structure. Alternatively, the spring member may be a deformable core member contained in a pliable loop structure having opposing end tabs that measure a tension load, and the electrical impedance may be a strain gage sensor bonded to the pliable loop structure. A further alternative may have the spring member be a deformable core member contained in a pliable loop structure having at least two opposing sides subjected to deforming pressure, where the electrical impedance is present in the deformable core member's structure by being fabricated with a distributed electrical impedence quality proportionally affected by deformation of the core member, and the electrical leads are connected to at least two opposing sides of the core member.

As a yet further example, there is an appliance system where the interconnecting member is configured with an elongation sensor for detecting and resolving the degree of linear motion between the anchor points. The interconnecting member may be capable of detecting and resolving the degree of rotational motion between the collar and the waist belt. Further, the interconnecting member may include an elongation motion static reset switch and cable assembly.

As an even yet further example, there may be a low force compliant sensor for a biofeedback system for converting a selected motion of a selected body joint into audible tones, where the sensor consists of a spring member that deforms under tension and reforms when released, with a measurable electrical impedance that varies with the degree of deformation applied to the spring member, and electrical leads by which the resistance can be measured. The compliant sensor may be a spring member consisting of a half oval shaped structure the ends of which are attached to an elastic base member subject to a tension load, where the electrical impedance consists of a strain gage sensor bonded to the half oval shaped structure. The spring member may consist of a deformable core member contained in a pliable loop structure having opposing end tabs subject to a tension load, where the electrical impedance consists of at least one strain gage sensor bonded to the pliable loop structure.

As yet another example, the compliant sensor may be a spring member consisting of a deformable core member contained in a pliable loop structure which has at least two opposing sides being subjected to deforming pressure, where the electrical impedance consists of the deformable core member fabricated with a distributed electrical impedence quality proportionally affected by deformation of the core member, and the electrical leads connected to the two opposing sides of the core member.

As still yet another example, the invention may consist of a biofeedback system for converting a selected motion of a selected body joint into audible tones, where the system includes a sensor for sensing body flexure, a signal processor and biofeedback module for receiving and processing input from the sensor and for transmitting one tone at a time from among a limited set of tones of stepped audio frequency, where each tone represents a different amount of body flexure. The system would include an adaptable appliance system for afixing the sensor in a suitable position to detect the selected motion.

An additional example of the invention is a biofeedback system where the appliance system consists of multiple components, each component having at least one coded anchor point, and the components are configurable on a user's body for establishing a suitable reference line for placement of the sensor relative to the subject motion. The multiple components can consist of a collar, a waist belt, and at least one interconnecting member attachable to the waist belt and to the collar at the coded anchor points, the sensor being attachable to the interconnecting member.

Another additional example is a biofeedback system where the sensor consists of a spring member that deforms under tension and reforms when released, a measurable electrical impedance that varies with the degree of deformation applied to the spring member, and electrical leads by which the resistance can be measured. The spring member consists of a half oval shaped structure the ends of which are attached to an elastic base member subject to a tension load. The electrical impedance consists of a strain gage sensor bonded to the half oval shaped structure.

Yet another example is a biofeedback system where the sensor consists of a spring member that deforms under tension and reforms when released, a measurable electrical impedance that varies with the degree of deformation applied to the spring member, and electrical leads by which the resistance can be measured. The spring member consists of a deformable core member contained in a pliable loop structure having opposing end tabs subject to a tension load, and the electrical impedance consists of at least one strain gage sensor bonded to the pliable loop structure.

What is claimed is:

1. A biofeedback system for sensing and signalling the occurrence and range of selectable twisting and bending body motions, comprising:
    a body appliance, said appliance comprising at least two separate components, each said component having at least one anchor point, each said anchor point having a unique identifier code,
    at least one gravity independent mechanically compliant motion sensor for sensing relative motion between selected said anchor points, at least two ends of said sensor attachable to respective anchor points on each of a selected two said components, said sensor comprising a compliant spring member mounted in tension with a measurable electrical output signal that varies with said tension and electrical leads by which said signal is measured, and
    means for monitoring said signal and generating therefrom as said feedback a limited set of tones of stepped audio frequency, each successive said tone representing an incrementally greater amount of said signal.

2. The biofeedback system of claim 1, said sensor comprising a piezoelectric element, said signal comprising a voltage signal.

3. The biofeedback system of claim 1, said sensor comprising an impedance, said signal comprising a system source of signal voltage in combination with said sensor.

4. The biofeedback system of claim 1, said body appliance comprising a collar and a waist belt, each having at least one said anchor point.

5. The biofeedback system of claim 3, said sensor comprising a half oval shaped structure and a strain gage, the ends of said half oval shaped structure being attached to in elastic base member, said strain gage being bonded to said half oval shaped structure.

6. The biofeedback system of claim 3, said sensor comprising a deformable core member contained in a pliable loop structure having opposing end tabs configured to be in tension, said impedance comprising at least one strain gage sensor bonded to said pliable loop structure.

7. The biofeedback system of claim 3, said sensor comprising a deformable core member contained in a pliable loop structure having at least two opposing sides subject to deforming under compression, said impedance comprising said core member fabricated with a distributed impedance quality proportionally affected by deformation of said core member, sail electrical leads connected to at least two opposing sides of said core member.

8. The biofeedback system of claim 4, further comprising a sensor means for detecting and resolving the relative degree of rotational motion as between selected said anchor points on said collar and said waist belt.

9. The biofeedback system of claim 4, further comprising an elongation motion static reset switch and cable sensor assembly connectable between selected said anchor points on said collar and said waist belt.

10. A biofeedback system for sensing and signalling the occurrence and range of twisting and bending body motions, comprising:
    a body appliance, said appliance comprising at least a collar component and a waist belt components, each said component having multiple distributed anchor points, each said anchor point having a unique identifier code,
    at least two gravity independent mechanically compliant motion sensors for sensing relative motion between selected said anchor points, two ends of each said sensor attachable to selected anchor points on each of a selected two said components, each said sensor comprising a measurable electrical signal that varies with said relative motion and electrical leads by which said signal is measured, and
    means for monitoring said signals and generating therefrom as aid feedback a limited set of tones of stepped audio frequency, each successive said tone representing an incrementally greater amount of a pre-selected combination of said signals.

11. The biofeedback system of claim 10, at least one said sensor comprising a piezoelectric element, said signal comprising a voltage signal.

12. The biofeedback system of claim 10, at least one said sensor comprising an impedance, said signal comprising a system source of signal voltage in combination with said sensor.

13. The biofeedback system of claim 10, one said sensor comprising means for detecting and resolving the relative degree of rotational motion as between said selected anchor points.

14. The biofeedback system of claim 10, one said sensor comprising an elongation motion static reset switch and cable assembly connectable between said selected anchor points.

* * * * *